United States Patent
Verstreken

(10) Patent No.: US 12,232,979 B2
(45) Date of Patent: Feb. 25, 2025

(54) TOOL FOR REAMING A CARPAL BONE

(71) Applicant: Zimmer, Inc., Warsaw, IN (US)

(72) Inventor: Frederik Marie Andre Jozef Verstreken, Schoten (BE)

(73) Assignee: Zimmer, Inc., Warsaw, IN (US)

( * ) Notice: Subject to any disclaimer, the term of this patent is extended or adjusted under 35 U.S.C. 154(b) by 684 days.

(21) Appl. No.: 17/434,060

(22) PCT Filed: Feb. 26, 2020

(86) PCT No.: PCT/US2020/019928
§ 371 (c)(1),
(2) Date: Aug. 26, 2021

(87) PCT Pub. No.: WO2020/176641
PCT Pub. Date: Sep. 3, 2020

(65) Prior Publication Data
US 2022/0133504 A1 May 5, 2022

(30) Foreign Application Priority Data
Feb. 27, 2019 (BE) .................................. 2019/5122

(51) Int. Cl.
*A61F 2/46* (2006.01)
*A61B 17/16* (2006.01)
(Continued)

(52) U.S. Cl.
CPC ........ *A61F 2/4606* (2013.01); *A61B 17/1686* (2013.01); *A61F 2002/30649* (2013.01); *A61F 2002/4258* (2013.01)

(58) Field of Classification Search
CPC . A61B 17/1686; A61B 17/1659; A61B 17/92; A61B 17/1664; A61B 17/1666; A61B 17/1684; A61F 2/4606
See application file for complete search history.

(56) References Cited

U.S. PATENT DOCUMENTS 4,106,128 A * 8/1978 Greenwald ........... A61F 2/3804
623/21.13
4,276,660 A * 7/1981 Laure .................... A61F 2/4241
623/21.16
(Continued)

FOREIGN PATENT DOCUMENTS

CN         116035649 A  *  5/2023
WO    WO-2020176641 A1     9/2020

OTHER PUBLICATIONS

"Belgian Application Serial No. BE2019/5122, Search Report and Written Opinion mailed Dec. 11, 2019", 10 pgs.
(Continued)

*Primary Examiner* — Alvin J Stewart
(74) *Attorney, Agent, or Firm* — SCHWEGMAN LUNDBERG & WOESSNER, P.A.

(57) ABSTRACT

Tool (1) for reaming a trapezium bone (2) when implanting a joint prosthesis (15, 16, 17) in the thumb (4), in which the tool has a head (5) and a handle (6) which extend along an axis (7), in which a connecting piece (8) is provided between the head and the handle, which connecting piece lies at a distance (9) from the axis in such a way that when rotating the head back and forth (13) using the handle the connecting piece moves at a distance from the thumb while the axis runs through the thumb.

12 Claims, 4 Drawing Sheets

(51) Int. Cl.
  *A61F 2/30* (2006.01)
  *A61F 2/42* (2006.01)

(56) References Cited

U.S. PATENT DOCUMENTS

| | | | | |
|---|---|---|---|---|
| 5,047,035 A * | 9/1991 | Mikhail | ............. | A61B 17/8847 606/92 |
| 5,318,570 A * | 6/1994 | Hood | ................ | A61B 17/8847 601/2 |
| 5,507,822 A * | 4/1996 | Bouchon | ............... | A61F 2/4241 623/21.16 |
| 5,702,469 A * | 12/1997 | Whipple | ............... | A61F 2/4241 623/21.15 |
| 5,800,551 A * | 9/1998 | Williamson | ....... | A61B 17/1778 623/19.11 |
| 5,906,210 A | 5/1999 | Herbert | | |
| 5,913,858 A | 6/1999 | Calandruccio et al. | | |
| 6,048,345 A * | 4/2000 | Berke | ................ | A61B 17/1659 606/177 |
| 6,364,910 B1 * | 4/2002 | Shultz | ............... | A61B 17/1684 606/86 R |
| 6,997,928 B1 * | 2/2006 | Penenberg | ......... | A61B 17/1746 606/81 |
| 7,621,921 B2 * | 11/2009 | Parker | ...................... | A61F 2/34 606/91 |
| 7,666,186 B2 * | 2/2010 | Harp | .................. | A61B 17/1624 606/85 |
| 7,976,548 B2 * | 7/2011 | Burgi | ................. | A61B 17/1659 74/544 |
| 8,092,453 B2 | 1/2012 | Warburton | | |
| 8,328,811 B2 * | 12/2012 | Myers | ...................... | B25G 1/04 606/79 |
| 8,398,650 B1 * | 3/2013 | Burgi | .................... | A61F 2/4609 606/91 |
| 8,926,621 B2 * | 1/2015 | Liang | .................. | A61F 2/4609 606/91 |
| 9,028,502 B2 * | 5/2015 | Burgi | .................... | A61F 2/4609 606/91 |
| 9,078,672 B1 * | 7/2015 | Rosse | ................ | A61B 17/1631 |
| 9,119,731 B2 * | 9/2015 | Burgi | ............... | A61F 2/4609 |
| 9,241,811 B2 * | 1/2016 | Davenport | ............ | A61F 2/4603 |
| 9,345,585 B2 * | 5/2016 | Black | ....................... | A61F 2/46 |
| 9,439,780 B2 * | 9/2016 | Witt | ..................... | A61F 2/4609 |
| 9,675,364 B2 * | 6/2017 | Fortin | ................. | A61B 17/1666 |
| 9,814,470 B2 * | 11/2017 | Weekes | .............. | A61B 17/1631 |
| 10,335,169 B2 * | 7/2019 | Phillips | .............. | A61B 17/1622 |
| 10,624,763 B2 * | 4/2020 | Conley | ................ | A61F 2/4609 |
| 10,856,888 B2 * | 12/2020 | Chenaux | ............. | A61B 17/162 |
| 11,160,564 B2 * | 11/2021 | Anthony | ............. | A61B 17/1659 |
| 11,160,565 B2 * | 11/2021 | Biegun | ............... | A61B 17/1631 |
| 2003/0220698 A1 * | 11/2003 | Mears | ...................... | B25B 7/02 623/22.4 |
| 2003/0229352 A1 * | 12/2003 | Penenberg | ......... | A61B 17/1746 606/81 |
| 2005/0038443 A1 * | 2/2005 | Hedley | ................ | A61B 17/162 606/86 R |
| 2005/0049623 A1 * | 3/2005 | Moore | ................ | A61B 17/1631 606/170 |
| 2005/0149047 A1 * | 7/2005 | Parry | .................... | A61F 2/4609 606/91 |
| 2007/0073302 A1 * | 3/2007 | Myers | ................. | A61B 17/1633 606/80 |
| 2007/0255418 A1 * | 11/2007 | Bonnard | ............... | A61F 2/4241 623/18.11 |
| 2007/0293869 A1 * | 12/2007 | Conte | ................. | A61B 17/1666 606/91 |
| 2008/0195106 A1 * | 8/2008 | Sidebotham | ....... | A61B 17/1617 606/80 |
| 2008/0215156 A1 * | 9/2008 | Duggal | .............. | A61B 17/1666 623/18.11 |
| 2008/0221698 A1 * | 9/2008 | Berger | .................. | A61F 2/4241 623/21.19 |
| 2008/0269908 A1 * | 10/2008 | Warburton | ......... | A61B 17/1782 623/21.15 |
| 2011/0082587 A1 * | 4/2011 | Ziaei | ..................... | A61F 2/4607 700/260 |
| 2012/0123419 A1 * | 5/2012 | Purdy | ................. | A61B 17/1615 606/83 |
| 2012/0197261 A1 * | 8/2012 | Rocci | .................. | A61B 17/1686 606/96 |
| 2013/0053904 A1 * | 2/2013 | Penenberg | ........... | A61B 17/175 606/86 R |
| 2013/0150859 A1 * | 6/2013 | Kehres | ............... | A61B 17/1617 606/81 |
| 2013/0158558 A1 * | 6/2013 | Preuss | .................... | A61B 17/92 606/91 |
| 2014/0018930 A1 * | 1/2014 | Oster | .................. | A61B 17/1739 623/23.39 |
| 2014/0303626 A1 * | 10/2014 | Winslow | ............ | A61B 17/1624 606/80 |
| 2015/0005776 A1 * | 1/2015 | Biegun | ............... | A61B 17/1631 606/85 |
| 2015/0297247 A1 * | 10/2015 | Seex | ................... | A61B 17/1604 |
| 2016/0175112 A1 * | 6/2016 | Pruvost | ............. | A61B 17/1633 606/81 |
| 2017/0196710 A1 * | 7/2017 | Behzadi | ............. | A61B 17/1659 |
| 2019/0254686 A1 * | 8/2019 | Wolford | ............ | A61B 17/1686 |
| 2020/0297356 A1 * | 9/2020 | Lualdi | ................ | A61B 17/1659 |
| 2021/0093465 A1 * | 4/2021 | Sweitzer | ............... | A61F 2/4612 |
| 2021/0113217 A1 * | 4/2021 | Lualdi | ............... | A61B 17/1684 |
| 2022/0104901 A1 * | 4/2022 | Lawrie | .............. | A61B 17/1659 |
| 2022/0202592 A1 * | 6/2022 | Clarke | ................. | A61F 2/4606 |
| 2022/0249252 A1 * | 8/2022 | Behzadi | ............. | A61F 2/4607 |
| 2022/0330972 A1 * | 10/2022 | Lualdi | ................ | A61B 17/162 |
| 2022/0409219 A1 * | 12/2022 | Lamba | .............. | A61B 17/1666 |
| 2023/0000500 A1 * | 1/2023 | Lamba | ............... | A61B 17/92 |

OTHER PUBLICATIONS

"International Application Serial No. PCT/US2020/019928, International Search Report mailed Jul. 13, 2020", 6 pgs.

"International Application Serial No. PCT/US2020/019928, Written Opinion mailed Jul. 13, 2020", 6 pgs.

"International Application Serial No. PCT US2020 019928, International Preliminary Report on Patentability mailed Sep. 10, 2021", 8 pgs.

"European Application Serial No. 20714067.4, Response Filed Apr. 17, 2022 to Communication Pursuant to Rules 161(2) and 162 EPC mailed Oct. 8, 2021", 15 pgs.

* cited by examiner

TOOL FOR REAMING A CARPAL BONE

This application is a U.S. National Stage Application under 35 U.S.C. 371 from International Application Serial No. PCT/US2020/019928, filed on Feb. 26, 2020, and published as WO 2020/176641 on Sep. 3, 2020, which claims priority under 35 U.S.C. 119 from Belgian Application Serial Number BE2019/5122, entitled "TOOL FOR REAMING A TRAPEZIUM BONE", filed on Feb. 27, 2019, which each application is incorporated herein by reference.

The invention relates to a tool for reaming a trapezium bone when implanting a joint prosthesis in the thumb.

Joint prostheses can be implanted for various reasons. A common reason is in arthritis when loss of cartilage and/or calcification prevents the normal working of the natural joint.

When a joint prosthesis is implanted it is advantageous to only affect the surrounding tissue to as small an extent as possible. This means that tendons and muscles as well as capsules and epidermal tissue are stretched as little as possible. This can be achieved relatively easily by keeping the thumb in as natural a position as possible when implanting the prosthesis.

The thumb is connected to the hand by means of a saddle joint. More particularly, a saddle joint is formed between the trapezium bone and the first metacarpal bone of the thumb. When a prosthesis is provided for this joint, typically a ball and socket joint is implanted. Because this type of prosthesis does not correspond to a natural joint type, a ball and socket joint rather than a saddle joint respectively, this prosthesis is called a non-anatomical prosthesis. In practice a cup will be implanted in the trapezium bone, and a stem will be inserted in the first metacarpal bone in which, at the end of the stem, a ball is provided which is compatible with the cup. By inserting the ball of the first metacarpal bone into the cup of the trapezium bone, the thumb gains a freedom of movement which corresponds almost completely to the freedom of movement which is also provided by the natural saddle joint.

In order to implant the cup in the trapezium bone, the trapezium bone must be reamed. The person skilled in the art understands that the reaming of the trapezium bone relates to the removing of material from the trapezium bone on the side of the joint, so that the cup fits accurately in the trapezium bone. In so doing, practice shows that it is advantageous to ream the trapezium bone as centrally as possible, and it also proves to be advantageous to ream the trapezium bone as straight as possible. Here straight relates to the angle of approach of the instrument in relation to the plane of the trapezium bone in which reaming is carried out. In practice it is difficult to ream the trapezium bone to an optimum extent.

The aim of the present invention is to provide a tool to make it easier to ream the trapezium bone.

For this, the invention provides a tool for reaming a trapezium bone when implanting a joint prosthesis in the thumb, in which the tool has a head and a handle which extend along an axis, in which there is a connecting piece between the head and the handle, this connecting piece being at a distance from the axis in such a way that when rotating the head back and forth with the handle, the connecting piece moves at a distance from the thumb, while the axis runs through the thumb.

The invention is based on the fact that the thumb is in the way when reaming the trapezium bone. In a conventional situation therefore the thumb is pushed aside and the trapezium bone is approached at an angle. By approaching the trapezium bone at an angle, it is, on the one hand, difficult to ream centrally. Furthermore the cup will fit less optimally in the reamed trapezium bone due to the angle. A further disadvantage is that by pressing on the side of the thumb the tissue around the joint has more pressure put on it and will result in a more negative effect on the implanting of the joint prosthesis. These disadvantages are solved by using the tool according to the invention. Namely, in the tool according to the invention a connecting piece is provided between the head of the tool and the handle, this connecting piece lying at a distance from the axis between the head and the handle. The connecting piece will therefore extend around the thumb, when the head of the tool and the handle of the tool are positioned straight in front of the trapezium bone with a straight angle of approach. The tool according to the invention enables the trapezium bone to be reamed without the thumb having to be pushed significantly to one side. Also, during reaming, the tool according to the invention makes it possible to approach the trapezium bone straight on. Turning the handle back and forth will directly result in the rotating back and forth of the head of the tool in line with the axis. As a result, it is easy to use the tool according to the invention. During the back and forth rotation, the connecting piece will move around the thumb. Tests have shown that it is significantly easier to ream a trapezium bone centrally and straight with the tool according to the invention.

Preferably the head will have a rasp on its outer surface. The rasp makes it easier to remove material from the trapezium bone while it is being reamed.

Preferably the head has a mainly spherical outer surface and the axis runs through a centre of the sphere. Furthermore, preferably the head is formed of a spherical cap, a surface of which is almost perpendicular to the axis. A spherical cap is defined as one of the two pieces of a ball which is intersected by a surface. Tests have shown that it is advantageous to implant the cup of the joint prosthesis in an opening which is hemispherical. Therefore the tool preferably has a spherical head. By using a spherical head, the depth of the cup can also be determined accurately.

The connecting piece preferably has several segments. More preferably the several segments contain, in sequence from the head to the handle, a first segment almost perpendicular to the axis, a second segment almost parallel to the axis and a third segment that is at a pre-determined angle to the axis. The specific sequence of segments in the connecting piece appears to be optimal for the use of the tool in reaming the trapezium bone. Because the first segment is perpendicular to the axis, the space required to position the head in relation to the reamed surface of the trapezium bone is minimal. The second segment and the third segment that is parallel and at an angle in relation to the axis, respectively, make it easier to use the tool.

Preferably a pre-determined angle is chosen so that, during the reaming of the trapezium bone, it is almost parallel to a first metacarpal bone of the thumb. More preferably the pre-determined angle is between 45° and 20°, more preferably between 38° and 25°, most preferably between 33° and 28° in relation to the axis. In particular by placing the third segment of the connecting piece in relation to the axis at an angle that is chosen in such a way that on using the trapezium bone the third segment is almost parallel to the first metacarpal bone of the thumb, use of the tool for reaming the trapezium bone is made significantly easier. The person skilled in the art is familiar with the preferred position of the thumb when implanting a joint prosthesis, and can therefore decide on an optimum pre-determined angle. As a result of this, the user of the tool is aided visually during use so that the central and straight reaming of the trapezium bone is made easier. The preferred position of the thumb is chosen in order to make access to the joint easier, namely maximum adduction and flexion of the first metacarpal.

Preferably the head is at a minimum distance from the handle of 5 cm, preferably at least a minimum of 6 cm. On the one hand the handle is preferably as close as possible to the head of the tool, on the other a sufficiently large distance has to be bridged by the connecting piece so that the tool does not collide with the thumb during the reaming of the trapezium bone. A minimum distance of 5 or 6 cm is optimal. Furthermore, preferably the head should be at a maximum distance from the handle of 12 cm, more preferably a maximum of 10 cm.

The invention also relates to a set of a tool according to the invention and a joint prosthesis for a thumb, in which the joint prosthesis is preferably a non-anatomical prosthesis with a ball which is provided on a stem, whereby the stem is shaped in such a way as to be fixed in the first metacarpal bone of the thumb and with a cup that is complementary to the ball and which is shaped in such a way as to be fixed in the trapezium bone of the thumb. In this, the head of the tool is preferably of a shape and dimensions that correspond to the outer shape and outer dimensions of the cup. The set according to the invention enables the non-anatomical joint prosthesis to be implanted.

The invention also relates to a method for implanting a non-anatomical prosthesis comprising:
  reaming of the trapezium bone using the tool of one of the previous claims;
  implanting the cup from the set according to one of the claims 10-12 in the reamed trapezium bone;
  implanting the ball from the set according to one of the claims 10-12 in the first metacarpal bone;
  positioning of the ball in the cup.

Preferably the reaming step consists of the back and forth rotation of the tool around the axis at an angle of between 20° and 180°, while the head of the tool is pressed against the trapezium bone. As a result of this the trapezium bone is reamed, that is to say that a space is created in the trapezium bone wherein the space has a shape corresponding to the head of the tool. This head has a shape and dimensions corresponding to an outer shape and outer dimensions of the cup of the joint prosthesis so that the cup of the joint prosthesis after reaming can be fixed directly in the trapezium bone.

The invention will now be described in greater detail on the basis of an embodiment shown in the drawing.

In the drawing:

FIG. 3A shows an enlarged view of the non-anatomical prosthesis of FIG. 3

In the drawing one and the same reference number is given to one and the same or an analogous element.

Figure 1:
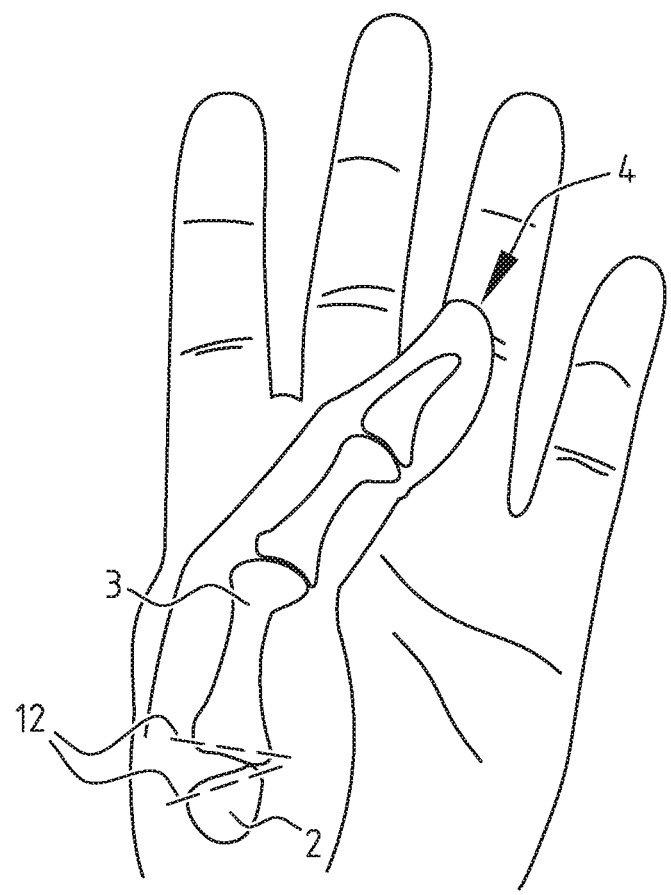
FIG. 1 shows a hand with a saddle joint in the thumb.

FIG. 1 shows a hand with a thumb 4. In the thumb the bones that are relevant to the invention are shown, more particularly the trapezium bone 2 and the first metacarpal bone 3. The trapezium bone 2 is also known as the os trapezium and the first metacarpal bone 3 is also known as the first metacarpal. FIG. 1 shows the natural joint between the trapezium bone 2 and the metacarpal bone 3 of the thumb 4. This is a saddle joint. If arthritis, calcification, rheumatism or inflammation occur, it may be necessary to implant a joint prosthesis. For this the thumb 4 is operated on, and a piece is sawn each out of the trapezium bone 2 and the metacarpal bone 3. FIG. 1 shows the preferred saw lines 12.

Figure 2:
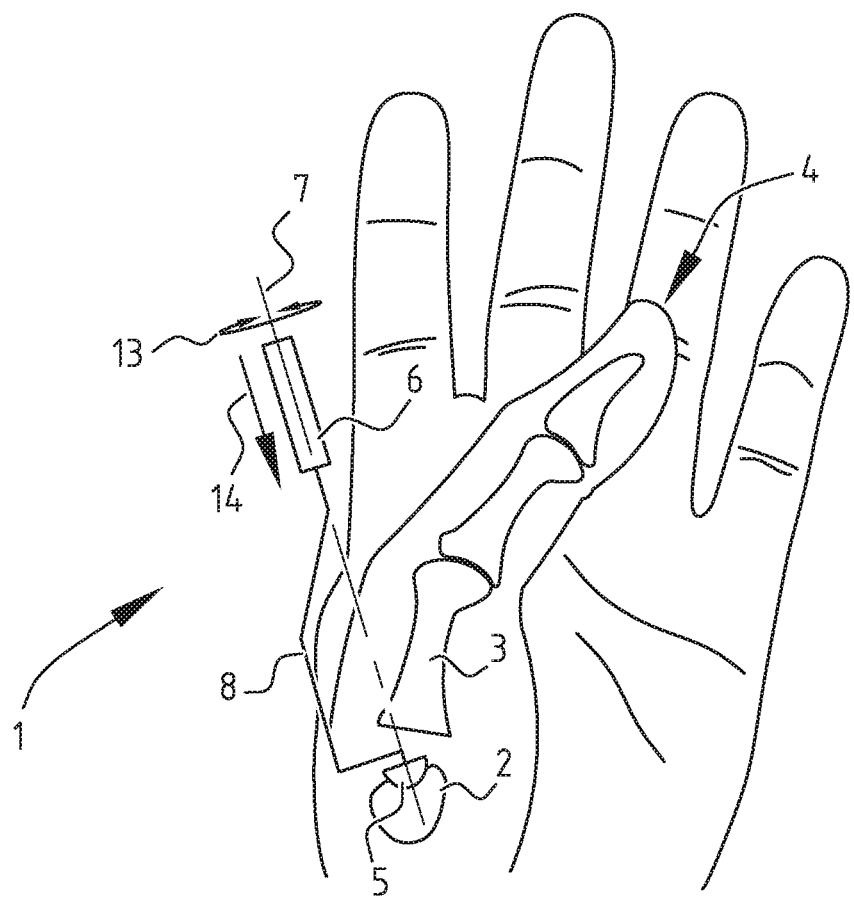
FIG. 2 shows a saddle joint that is prepared with a tool according to a preferred embodiment of the invention for implanting the prosthesis.

FIG. 2 shows the same thumb 4 as in FIG. 1, in which the trapezium bone 2 and the metacarpal bone 3 are prepared, that is to say that a piece of the respective bones is sawn according to the saw lines in FIG. 1. FIG. 2 shows how a tool 1 is used to ream the trapezium bone 2. Reaming is defined as the forming of a cup-like cavity in the trapezium bone. The cup-like cavity preferably has as constant a shape as possible and is preferably created as centrally as possible in the trapezium bone 2.

To ream the trapezium bone 2 a tool 1 is provided. This tool 1 has a head 5 which is shaped in such a way as to ream the trapezium bone 2. This is described in further detail on the basis of FIG. 4, The tool 1 is formed with a connecting piece 8 between the handle 6 and the head 5. Handle 6 and head 5 are formed around an axis 7 in such a way that the tool 1 is easy to use. Tool 1 can be used in the same way as a screwdriver is used. In a screwdriver too the handle is in line with the head in such a way that using the handle, more particularly the rotating of it, is directly accompanied by proportionate rotation of the head. However, as shown in FIG. 2, the direct connection between the head 5 and the handle 6 is blocked by the thumb 4. The connecting piece 8 is shaped in such a way that it is at a distance from the axis, further explained on the basis of FIG. 4, in order to extend around the thumb 4. This enables the trapezium bone 2 to be reamed easily.

When reaming the trapezium bone 2 the head 5 is positioned centrally against the sawn surface of the trapezium bone 2. By using the handle 6 the tool 1 can be positioned and used. The tool 1 is typically rotated back and forth, illustrated in the figure with arrow 13, in which the connecting piece 8 gradually moves around the thumb 4. During rotation 13 a pressure 14 is also applied in the direction of the head 5 in such a way that the head 5 moves in the trapezium bone 2 as a result of the rotation 13 and the pressure 14. The head 5 is typically provided with a rasp so that material from the trapezium bone 2 is rasped away and therefore the head 5 can be inserted in the trapezium bone. During the reaming of the trapezium bone 2 the axis 7 extends typically from the thumb 4 while the connecting piece 8 extends around the thumb 4.

Figure 3:
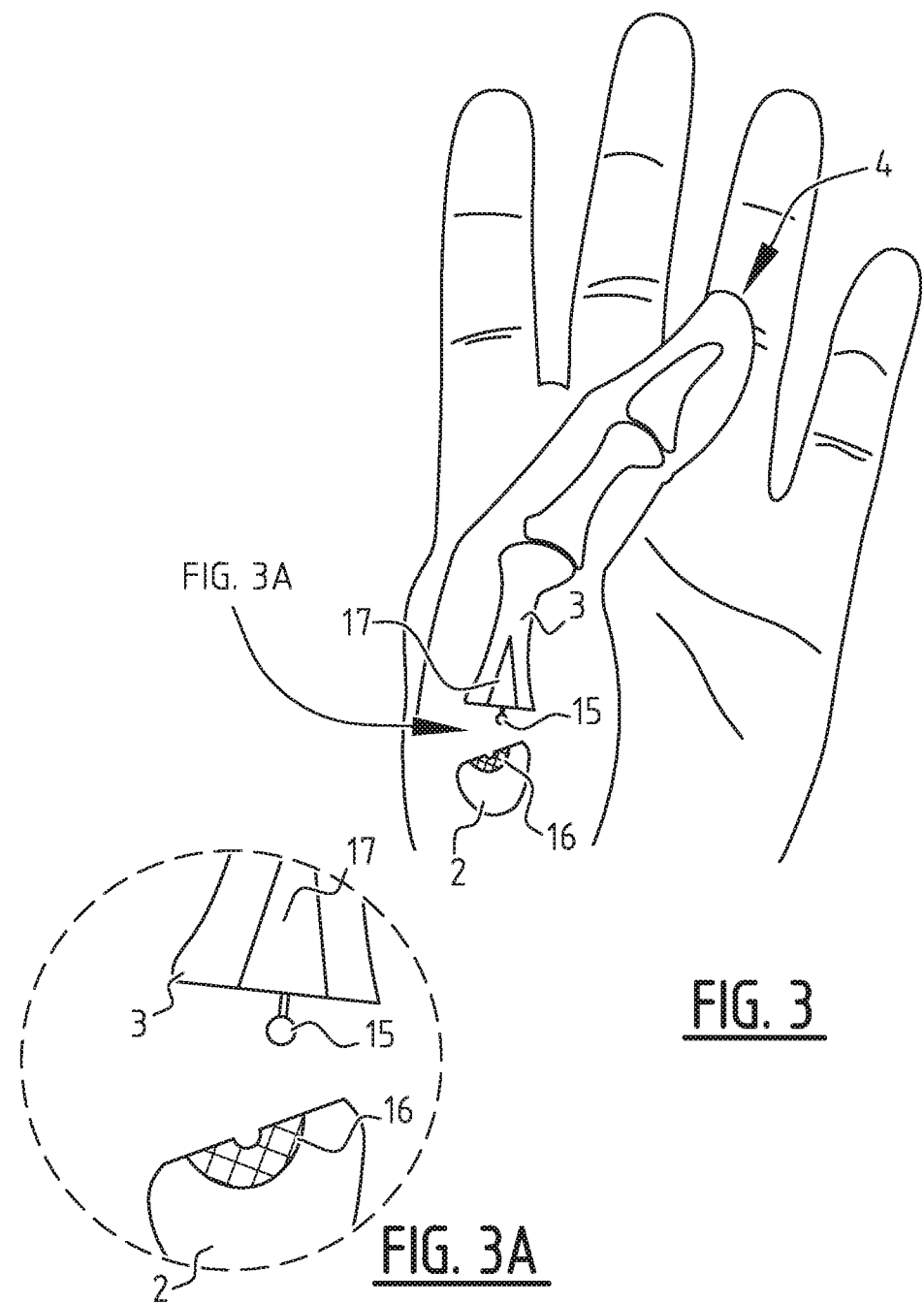
FIG. 3 shows a joint with a non-anatomical prosthesis.

FIG. 3 shows the thumb 4 provided with the joint prosthesis. The joint prosthesis has a cup 16 at the trapezium bone 2. This cup has an outer surface that is connected in the cavity that is formed by the reaming of the trapezium bone 2. The outer surface of the cup 16 therefore preferably corresponds to the outer surface of the head 5 of the tool 1. The cup 16 is fixed in a known manner in the trapezium bone, and this step is therefore not described in further detail. At the first metacarpal bone 3 the joint prosthesis is provided with a stem 17 which is at least partially inserted in the metacarpal bone and a ball 15 which extends from the stem 17 in the direction of the trapezium bone 2. The ball 15 and the cup 16 are compatible in such a way that a ball and socket joint is formed when implanting the elements of the prosthesis. The stem 17 with the ball 15 as well as the cup 16 are known and are therefore not described in further detail.

Figure 4:
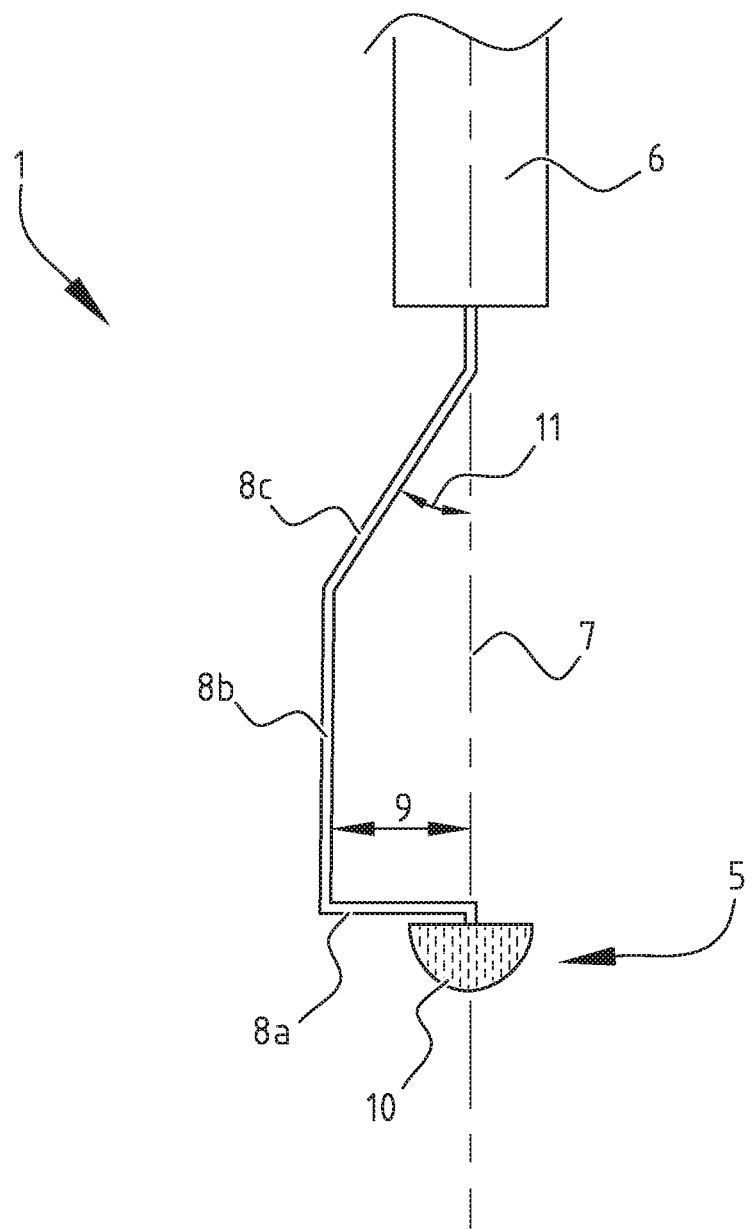
FIG. 4 shows a tool according to a preferred embodiment of the invention.

FIG. 4 shows a detail of tool 1. On the left side of the figure part of the handle 6 is shown and on the right side of the figure the head 5 is shown. The handle 6 can be shaped in different ways to assist with the use of the tool 1. The head 5 has an outer surface 10. The outer surface 10 is preferably spherical. More particularly the outer surface 10 is formed by a spherical cap. The outer surface 10 is preferably provided with a rasp. More particularly, projections are provided on the outer surface 10, in which the projections have a previously determined size and are of a previously determined sharpness, the purpose being to scrape away bone tissue when the head 5 is moved against the trapezium bone 2. The person skilled in the art will understand that various rasps are known for removing bone tissue, and that a known rasp can be used on the outer surface 10 of the tool 1.

Between the handle 6 and the head 5 extends a connecting piece 8. FIG. 4 shows how the connecting piece 8 has several segments. The first segment is indicated with reference number 8a, the second segment is indicated with reference number 8b and the third segment is indicated with reference number 8c. The first segment 8a is formed at the head 5, and extends virtually perpendicularly to the axis 7. The second segment 8b extends virtually parallel to the axis 7. The second segment 8b is at a distance 9 from axis 7. This distance 9 is chosen in such a way that, when using the tool 1, the connecting piece extends around the thumb 4.

The connecting piece 8 also has a third segment 8c. This third segment extends at an angle 11 between the second segment Sb and the handle 6. This angle 11 is chosen in such a way that when using the tool for reaming a trapezium bone 2, the third segment extends virtually parallel to an outer surface of the thumb 4 in the preferred position. In the preferred position the thumb displays maximum adduction and flexion of the first metacarpal. This preferred position is chosen to make access to the joint easy. This is illustrated in FIG. 2, from which it is clear that the third segment 8c extends virtually parallel to the thumb 4. For the user of the tool this forms a visual guide for optimum reaming of the trapezium bone 2. The angle 11 is preferably greater than 20 degrees, more preferably greater than 25 degrees and is preferably less than 50 degrees, more preferably less than 40 degrees. Most preferably the angle is around 30 degrees.

From FIG. 4 it is also clear that the head 5 is not necessarily connected to the first segment Ra of the connecting piece 8a, but that between the head 5 and the first segment 8a a further connecting piece can be formed. This further connecting piece can also be seen as the neck to which the head 5 is fixed. FIG. 4 also shows how the third segment Sc of the connecting piece is not necessarily directly connected to the handle 6, but that a further connecting piece can extend between the handle 6 and the third segment Sc. This further connecting piece then extends typically along the axis 7 as an extension of the handle 6.

Below are explained the steps for implanting a joint prosthesis using a tool as described above. This method comprises at least one or more of the steps described below:

making a dorsal incision between the extensor pollicis longus EPL tendon and the extensor pollicis brevis EPB tendon;
pulling back the radial artery in order to free up access to the joint;
making an incision in the capsule of the joint;
loosening the capsule at the first metacarpal basis;
exposing the joint;
sawing away and removing the base of the first metacarpal bone according to a saw line;
sawing away and removing the end and/or the part of the joint of the trapezium bone according to a saw line;
removing osteophytes;
hollowing out the first metacarpal hone;
implanting a test stem in the first metacarpal bone;
reaming the trapezium bone using the tool 1 described above;
placing cup 16 in the reamed trapezium bone 2;
placing a test ball 13 on the test stem 17 in order to determine the optimum distance between the ball 15 and the stem 17;
testing the stability of the joint;
placing the definitive stem with the ball and making the joint work;
repairing the capsule;
closing the incision.

On the basis of the description above the person skilled in the art will understand that the invention can be carried out in different ways and on the basis of various principles. As such the invention is not limited to the embodiments described above. The embodiments described above, as well as the figures, are only by way of illustration and only serve to increase understanding of the invention. The invention will therefore not be limited to the embodiments described here but is defined in the claims.

The invention claimed is:

1. A tool for reaming a trapezium bone when implanting a joint prosthesis in the thumb, the tool comprising:
    a head;
    a handle extending along an axis; and
    a connecting piece provided between the head and the handle, the connecting piece including a first segment virtually perpendicular to the axis a second segment virtually parallel to the axis, and a third segment which is at a previously determined angle to the axis, wherein the connecting piece lies at a distance from the axis in such a way that when rotating the head back and forth using the handle, the connecting piece moves at a distance from the thumb while the axis runs through the thumb.

2. The tool according to claim 1, wherein the head contains a rasp on its outer surface.

3. The tool according to claim 1, wherein the head has a mainly spherical outer surface and in which the axis runs through a centre of the sphere.

4. The tool according to claim 3, wherein the head is formed of a spherical cap from which a surface stands virtually perpendicular to the axis.

5. The tool according to claim 1, wherein the previously determined angle is chosen in order, during the reaming of the trapezium bone, to lie virtually parallel to a first metacarpal bone of the thumb, in a preferred position of the thumb.

6. The tool according to claim 5, wherein the previously determined angle is between 45 degrees and 20 degrees.

7. The tool according to claim 1, wherein the head lies at a minimum distance from the handle of 6 cm.

8. A system comprising the tool according to claim 1 and a joint prosthesis for a thumb.

9. The system according to claim 8, wherein the joint prosthesis is a non-anatomical prosthesis with a ball which is provided on a stem, wherein the stem is shaped in order to be fixed in the first metacarpal bone of the thumb and with a cup that is complementary to the ball and which is shaped in order to be fixed into the trapezium bone of the thumb.

10. The system according to claim 9, wherein the head of the tool has a shape and dimensions that correspond to an outer shape and outer dimensions of the cup.

11. A method for the implantation of a non-anatomical prosthesis including a ball and a cup, the method comprising:
   reaming a trapezium bone using the tool of claim 1;
   implanting the cup in the reamed trapezium bone;
   implanting the ball in a first metacarpal bone; and
   positioning the ball in the cup.

12. The method according to claim 11, wherein the step of reaming comprises the rotation back and forth of the tool around the axis at an angle between 20 degrees and 180 degrees while the head of the tool is pressed against the trapezium bone.

* * * * *